(12) United States Patent
Wang et al.

(10) Patent No.: US 9,730,916 B2
(45) Date of Patent: Aug. 15, 2017

(54) NUTRITIONAL COMPOSITION AND METHOD FOR IMPROVING HEART FAILURE

(71) Applicant: Chang Gung Memorial Hospital, Keelung, Keelung (TW)

(72) Inventors: Chao-Hung Wang, Keelung (TW); Ming-Shi Shiao, Tao-Yuan (TW); Mei-Ling Cheng, Tao-Yuan (TW)

(73) Assignee: Chang Gung Memorial Hospital, Keelung, Keelung (TW)

( * ) Notice: Subject to any disclaimer, the term of this patent is extended or adjusted under 35 U.S.C. 154(b) by 41 days.

(21) Appl. No.: 14/631,620

(22) Filed: Feb. 25, 2015

(65) Prior Publication Data

US 2015/0238464 A1   Aug. 27, 2015

Related U.S. Application Data

(60) Provisional application No. 61/945,427, filed on Feb. 27, 2014.

(51) Int. Cl.

| | |
|---|---|
| *A61K 31/4172* | (2006.01) |
| *A61K 33/06* | (2006.01) |
| *A61K 33/30* | (2006.01) |
| *A61K 31/198* | (2006.01) |
| *A61K 31/716* | (2006.01) |
| *A61K 31/05* | (2006.01) |
| *A61K 31/205* | (2006.01) |
| *A61K 31/122* | (2006.01) |
| *A61K 33/34* | (2006.01) |
| *A61K 33/04* | (2006.01) |
| *A61K 31/07* | (2006.01) |
| *A61K 31/51* | (2006.01) |
| *A61K 31/525* | (2006.01) |
| *A61K 31/675* | (2006.01) |
| *A61K 31/519* | (2006.01) |
| *A61K 31/714* | (2006.01) |
| *A61K 31/375* | (2006.01) |
| *A61K 31/355* | (2006.01) |
| *A61K 31/592* | (2006.01) |
| *A61K 31/593* | (2006.01) |
| *A61K 31/455* | (2006.01) |
| *A61K 31/132* | (2006.01) |
| *A61K 31/19* | (2006.01) |
| *A61K 31/4415* | (2006.01) |
| *A61K 31/59* | (2006.01) |

(52) U.S. Cl.
CPC .......... *A61K 31/4172* (2013.01); *A61K 31/05* (2013.01); *A61K 31/07* (2013.01); *A61K 31/122* (2013.01); *A61K 31/132* (2013.01); *A61K 31/19* (2013.01); *A61K 31/198* (2013.01); *A61K 31/205* (2013.01); *A61K 31/355* (2013.01); *A61K 31/375* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/59* (2013.01); *A61K 31/592* (2013.01); *A61K 31/593* (2013.01); *A61K 31/675* (2013.01); *A61K 31/714* (2013.01); *A61K 31/716* (2013.01); *A61K 33/04* (2013.01); *A61K 33/06* (2013.01); *A61K 33/30* (2013.01); *A61K 33/34* (2013.01)

(58) Field of Classification Search
CPC .. A61K 2300/00; A61K 33/06; A61K 31/195; A61K 31/28; A61K 31/198; A61K 31/10; A61K 31/05; A61K 31/191; A61K 31/194; A61K 31/4172; A61K 33/14; A61K 9/20; A61K 9/2027; A61K 9/284; A61K 31/07; A61K 31/122; A61K 31/132; A61K 31/185; A61K 31/19; A61K 31/205; A61K 31/355; A61K 31/375; A61K 31/4415; A61K 31/455; A61K 31/51; A61K 31/525

See application file for complete search history.

(56) References Cited

U.S. PATENT DOCUMENTS

2006/0281822 A1\* 12/2006 Appleton ............... A61K 31/10
                                                              514/709

\* cited by examiner

*Primary Examiner* — Debbie K Ware

(74) *Attorney, Agent, or Firm* — WPAT, P.C., Intellectual Property Attorneys; Anthony King

(57) ABSTRACT

The disclosure provides a nutritional composition for improving a patient with heart failure; the nutritional composition is consisting of therapeutically effective high amounts of leucine and histidine. The disclosure also provides the nutritional supplement comprising the nutritional composition, which may be a beverage product, a dietary supplement or food. The disclosure further provides a method of using the nutritional supplement for treating patients with heart failure.

21 Claims, 1 Drawing Sheet

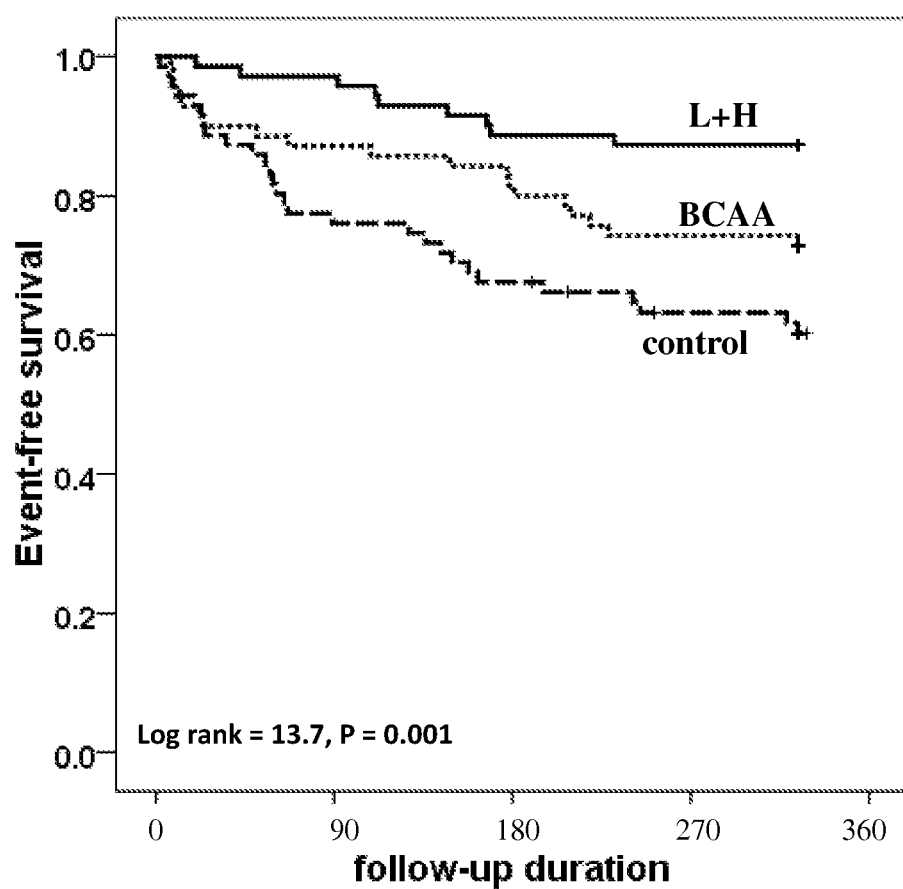

NUTRITIONAL COMPOSITION AND METHOD FOR IMPROVING HEART FAILURE

CROSS-REFERENCE TO RELATED APPLICATIONS

This application claims a priority of Provisional Application No. 61/945,427, filed on 27 Feb. 2014, the disclosure of which is incorporated by reference herein in its entirety.

BACKGROUND OF THE INVENTION

1. Field of the Invention

The present invention relates to a nutritional composition for individuals suffering from cardiovascular disease, and more particular, to acute or chronic heart failure.

2. The Prior Arts

Heart failure (HF) is a complex clinical syndrome that represents the end stage of various cardiac diseases, with a dismal prognosis that is worse even than many types of cancer. The estimated cost of HF is currently between 1-2% of the total healthcare spending in developed economies and is expected to rise. Nevertheless, short- and long-term HF-related re-hospitalization and mortality remain high. Current treatments focus on drug therapies and devices (implantable defibrillators and resynchronization). However, they do not 'cure' the condition, and they are not truly 'disease modifying' for HF.

HF is considered to have a multifactor pathogenesis in which peripheral circulatory insufficiency, autonomic imbalance, activation of the renin-angiotensin system, inflammation, oxidative stress, immune system activation, and insulin resistance are intertwined in a complex manner. The metabolic abnormalities resulting from these complex factors can be linked to long-term myocardial dysfunction. In addition, these metabolic processes have been shown to affect other organs, including skeletal muscle, leading to fatigue and physical dysfunction of patients with HF. Moreover, complications of metabolic diseases such as anemia, diabetes mellitus, renal dysfunction, and cardiac cachexia also greatly influence the prognosis of HF.

SUMMARY OF THE INVENTION

Accordingly, there is a need of nutritional support for improving a patient with heart failure; the present invention fulfills the need to provide a nutritional composition, a nutritional supplement containing the nutritional composition and a method of using the nutritional supplement in treating patient with heart failure.

One aspect of the present invention is related to a nutritional composition for improving a patient with heart failure, consisting of therapeutically effective high amounts of leucine and histidine, wherein the ratio of histidine:leucine is 1:5 to 1:11, and the amount of leucine is between 4.0 g and 12.0 g.

Another aspect of the present invention is related to a nutritional supplement for improving a patient with heart failure comprising above-mentioned nutritional composition.

In one embodiment, the nutritional supplement further comprises isoleucine and valine, and the nutritional composition is 33.0%-65.0% (w/w), isoleucine is 6.8%-12.0% (w/w), valine is 12.5%-23.0% (w/w) per unit dose of the nutritional supplement, the unit dose corresponding to per day.

In one embodiment, the nutritional supplement further comprises at least one selected from the group consisting of saccharide, mineral, vitamin, polyphenol, L-carnitine, Co-enzyme Q10 niacin and β-hydroxy-β-methylbutyrate (HMB), the saccharide is a β-glucan-like polysaccharide from *Auricularia polytricha* or giant kelp; or the saccharide is an oligosaccharide, and the oligosaccharide is fructo-oligosaccharide.

In one embodiment, the polyphenol is resveratrol.

In one embodiment, the mineral is selected from the group consisting of calcium, magnesium, zinc, copper and selenium.

In one embodiment, the vitamin is selected from the group consisting of vitamin A, vitamin B6, vitamin B12, vitamin C, vitamin E, vitamin D, thiamine, riboflavin and folate.

In one embodiment, the nutritional supplement has no medium-chain triglycerides, tyrosine, spermidine, spermine, or phenylalanine.

In one embodiment, the nutritional supplement is in a form selected from the group consisting of powder, liquid, and ready-to use.

Another aspect of the present invention is related to a method of improving a heart failure in a patient, comprising administering to the patient a nutritional supplement comprising a therapeutically effective amount of above-mentioned composition.

In one embodiment, the nutritional supplement is administered orally per day.

In one embodiment, the patient suffers acute or chronic heart failure.

In one embodiment, when administered to the patient, the nutritional supplement increase the skeletal muscle mass, the left ventricular ejection fraction, hemoglobin and 6-minute walking distance.

In one embodiment, the nutritional composition is 33.0%-65.0% (w/w), isoleucine is 6.8%-12.0% (w/w), valine is 12.5%-23.0% (w/w) per unit dose of the nutritional supplement, the unit dose corresponding to per day.

In one embodiment, the nutritional supplement further comprises at least one selected from the group consisting of polysaccharide, mineral, vitamin, polyphenol, L-carnitine, Co-enzyme Q10, niacin and β-hydroxy-β-methylbutyrate (HMB).

In one embodiment, the nutritional supplement has no medium-chain triglycerides, tyrosine, spermidine, spermine, or phenylalanine.

The patients with HF are supplied with the nutritional composition of the present invention have higher blood leucine, histidine, albumin, and hemoglobin levels; also have a longer 6-min walking distance, increased skeletal muscle mass, left ventricular ejection fraction, and have a lower HF-related re-hospitalization rate. Therefore, nutritional support will be considered to be a new therapeutic target for HF.

The detailed technology and above preferred embodiments implemented for the present invention are described in the following paragraphs accompanying the appended drawings for people skilled in this field to well appreciate the features of the claimed invention.

BRIEF DESCRIPTION OF THE DRAWINGS

FIGURE is a diagram showing the heart failure-related event-free survival rate included the rate of re-hospitalization; the "L+H" group: patients' food was additionally supplied with high amounts of leucine (8.3±3.2 g/day) and histidine (1.5±0.5 g/day); the branch chain amino acid (BCAA) group: patients' food was additionally supplied with Leucine (4.3±0.5 g of Leucine/day, 2.2±0.3 g of Isoleucine/day, and 4.4±0.4 g of Valine/day); and the control groups: no specific increase in their nutritional amount besides their usual intake.

DETAILED DESCRIPTION OF THE PREFERRED EMBODIMENT

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention.

As used herein, numerical quantities given herein are approximate, all the clinical and laboratory data generally mean within 20 percent, preferably within 10 percent, and more preferably within 5 percent of a given value or range.

Nutrients are not drugs and, as recently emphasized, 'nutrition is not pharmacology'. This is most important, because the nutritional approach necessarily involves multiple factors, and because most nutrients are biologically active in the body through synergistic effects. Metabolomics-based nutritional composition and micronutrient supplementation should be combined in patients with overt heart failure (HF). The essence of designing a nutritional composition specific for HF takes advantage of the findings derived from the complicated interactions of metabolic pathways in HF.

The effect of a metabolomics-based nutritional composition in HF patients can definitely improve the symptoms, quality of life, and disease status, which may be associated with better outcomes, including lower rates of re-hospitalization, and mortality. In addition to the benefits of saving a lot of medical cost related to HF care, the developed knowledge can also produce numerous scientific values.

So far, the etiology of a substantial proportion of heart failure patients remains unexplained according to current knowledge on cardiovascular risk factors. Regardless of the heterogeneous etiologies, the development of heart failure is causally related to the inability of the heart to meet the metabolic demands of the body. The accompanying changes in global metabolism are suggestive of clinical application of heart failure-specific metabolism for diagnostic and prognostic purposes. Current staging on heart failure is based on the consensus developed from American College of Cardiology and the American Heart Association (ACC/AHA), instead of pathogenic mechanism. The ACC/AHA classification of heart failure has four stages. For example, stage A refers to those at risks for heart failure, but who have not yet developed structural heart changes (diabetics, those with coronary disease without prior infarct). Stage B refers to individuals with structural heart disease (i.e. reduced ejection fraction, left ventricular hypertrophy, chamber enlargement), however no symptoms of heart failure have ever developed. Stage C means that patients who have developed clinical heart failure. Stage D is meant to patients with refractory heart failure requiring advanced intervention (biventricular pacemakers, left ventricular assist device, or transplantation). In addition to heart failure staging by the definition of ACC/AHA, there is another classification to define the functional status heart failure, called New York heart Association functional classification (class I to class IV). This classification relates symptoms to everyday activities and the patient's quality of life. Class I: no limitation of physical activity. Ordinary physical activity does not cause undue fatigue, palpitation, or dyspnea (shortness of breath). Class II: slight limitation of physical activity. Comfortable at rest, but ordinary physical activity results in fatigue, palpitation, or dyspnea. Class III: marked limitation of physical activity. Comfortable at rest, but less than ordinary activity causes fatigue, palpitation, or dyspnea. Class IV: unable to carry out any physical activity without discomfort; symptoms of cardiac insufficiency at rest. If any physical activity is undertaken, discomfort is increased.

Example 1 Metabolomics-Based Nutritional Assessment

In the present invention, taking advantage of the high throughput and the potential of developing multiple biomarkers, metabolomics is a scientific platform of identifying metabolic signatures for patients at status from pre-HF to advanced HF, independent of traditional risk factors. A thorough understanding of HF-associated metabolic perturbation, together with advances in nutrigenomic research, potentially benefits the development of personalized therapeutic strategy.

HF stage C is classified according to ACC/AHA HF classification system. Patients at stage C are those hospitalized due to acute or decompensated chronic HF, and aged 20-85 years. Patients with systolic and diastolic HF are included. Meanwhile, normal controls are aged 20-85 years, and have no significant systemic disease, such as hypertension, diabetes mellitus, or coronary artery disease. They were not on any medications, and had a left ventricular ejection fraction (LVEF) of >60%.

Plasma concentrations of metabolites, such as histidine, phenylalanine, ornithine, spermine, spermidine, taurine, and phosphatidylcholines, show significant differences among patients at different stages of HF. Combinations of metabolites serve as good biomarkers, which are as equally effective as the conventional biomarker B-type natriuretic peptide (BNP) for diagnosis, and are better for prognosis. On the other hand, the changes in metabolites common to HF patients with different etiologies suggest that HF development may involve a universal metabolic disturbance. A number of pathways, namely glutamate-ornithine-proline pathway, polyamine synthesis, dopamine pathway, and phosphatidylcholines synthesis, are specifically affected during HF progression.

In the present invention, quantification of metabolites was performed by methods described as follows. To 50-μL plasma, 200 μL acetonitrile (ACN) was added. The mixture was vortexed for 30 s, sonicated for 15 min and centrifuged at 10,000×g for 25 min. The supernatant was collected into a separate glass tube. The pellets were re-extracted with 200 μL 50% methanol. The aqueous methanolic supernatant and acetonitrile supernatant were pooled and dried in a nitrogen evaporator. The residues were saved and stored at −80° C. For metabolomics analysis, the residues were suspended in 100 μL of 95:5 water/acetonitrile and centrifuged at 14,000×g for 5 min. The clear supernatant was collected for LC-MS analysis.

Liquid chromatographic separation was achieved on a 100 mm×2.1 mm Acquity 1.7-μm C8 column (Waters Corp., Milford, USA) using an ACQUITY™ UPLC system (Waters Corp., Milford, USA). The column was maintained at 45 □, and at a flow rate of 0.5 ml/min. Samples were eluted from LC column using a linear gradient: 0-2.5 min: 1-48% B; 2.5-3 min: 48-98% B; 3-4.2 min: 98% B; 4.3-6 min: 1%

B for re-equilibration. The mobile phases were 0.1% formic acid (solvent A) in water and 0.1% formic acid in acetonitrile (solvent B).

The eluent was introduced into the TOF MS system (SYNAPT G1 high-definition mass spectrometer, Waters Corp., Milford, USA) and operated in an ESI-positive ion mode. The conditions were as follows: desolvation gas was set to 700 l/h at a temperature of 300° C., cone gas set to 25 l/h, and source temperature set at 80° C. The capillary voltage and cone voltage were set to 3,000 V and 35 V, respectively. The MCP detector voltage was set to 1,650 V. The data acquisition rate was set at 0.1 s with a 0.02 s interscan delay. The data were collected in centroid mode from 20 to 990 m/z. For accurate mass acquisition, a lock-mass of sulfadimethoxine at a concentration of 60 ng/ml and a flow rate of 6 □l/min (an [M+H]$^+$ ion at 311.0814 Da in ESI-positive mode) were processed.

Raw mass spectrometric data were processed using MassLynx V4.1 and MarkerLynx software (Waters Corp., Milford, USA). The intensity of each mass ion was normalized with respect to the total ion count to generate a data matrix that included the retention time, m/z value, and the normalized peak area. Exact molecular mass data were then submitted for database searching, either in-house or using the online HMDB (The Human Metabolome Database) and KEGG (Kyoto Encyclopedia of Genes and Genomes) databases.

The key metabolites showing significant differences in abundance between stage C according to ACC/AHA HF classification system and normal controls are histidine, phenylalanine, spermidine and phosphatidylcholine C34:4. histidine and phosphatidylcholine C34:4 significantly decreased, but phenylalanine and spermidine significantly increased in HF patients. These metabolites are mapped to biochemical pathways. Anomalous fluxes through these metabolic pathways may demonstrate important pathogenic roles. Intriguingly, levels of histidine and phosphotidylcholine C34:4 increased, while levels of phenylalanine and Spermidine decreased in patients who were in better medical conditions.

The metabolomics results demonstrated important clinical applications for prognosis in addition to diagnosis. The metabolite set consisting of 4 metabolite components gives a better prognostic value than the conventional biomarker BNP. This metabolic profile covered different aspects of pathogenesis. For instance, total dimethylarginine/arginine ratio is indicative of endothelial dysfunction; spermidine is probably indicative of toxicity of cardiomyocytes; butyrylcarnitine is indicative of anomalous lipid metabolism; and the total essential amino acids is indicative of malnutrition. Also, these findings raise the possibility of applying adjunctive therapy for severe HF patients through nutritional support on their metabolism.

Metabolic abnormalities represent a status related to HF, rather than the acute insult of HF. BNP level is dramatically decreased after the acute phase of HF, and then remained relatively low throughout the following 12 months. In the metabolic profile, there was a similar pattern. However, an interesting trend was noted that the metabolic profile at 12 months was worsening compared to the profile at 6 months. It is to be elucidated in a long-term follow up whether a subclinical worsening of metabolic disturbance precedes the future clinical deterioration. These data lend further support to the specificity of estimating HF status by metabolic profiles, and investigations on the value of initiating early nutritional support for subjects at pre-HF stage or at the recovery stage after acute or decompensated HF.

Actually, the value of estimating metabolic profiles in HF is far beyond diagnosis only. The information derived from the metabolomics abnormalities may provide the best platform to design a metabolomics-based nutritional regimen for HF patients, and also provide a sensitive metabolomics-based profile to define the effect in response to any nutritional composition.

Example 2 Design of Metabolomics-Based Nutritional Composition

In the present invention, based on metabolomics findings, providing a nutritional composition to improve the metabolomics-based HF-related abnormalities, nutritional status, functional status, and health-related quality of life, and decrease the event rates of HF-related re-hospitalization. This work is critically relevant to bench to bedside application, and will be beneficial to patient care and economy.

A few different regimens of nutrition support for HF patients are listed as follows:

Nutritional composition: high amounts of leucine and histidine, the ratio of histidine:leucine is 1:5 to 1:11, and the amount of leucine is between 4.0 g and 12.0 g. The nutritional supplement is as follows, and the nutritional composition or the nutritional supplement is in a form selected from the group consisting of powder, liquid, and ready-to use.

Supplement 1: isoleucine and valine.
Supplement 2: saccharide, such as β-glucan-like polysaccharides from as *Auricularia polytricha* or giant kelp and fructo-oligosaccharide.
Supplement 3: polyphenols, such as resveratrol.
Supplement 4: L-carnitine.
Supplement 5: Co-enzyme Q10.
Supplement 6: micronutrients contains niacin, calcium, magnesium, zinc, copper, selenium, vitamin A, thiamine, riboflavin, vitamin B6, folate, vitamin B12, vitamin C, vitamin E and vitamin D.
Supplement 7: β-hydroxy-β-methylbutyrate (HMB), HMB is a metabolite of leucine. HMB also has effects on increasing muscle production, and inhibiting muscle breakdown.

In the present invention, the nutritional composition is respectively supplemented with Supplement 1 to 7, which including an additional requirement without the amount of medium-chain triglycerides, tyrosine, spermidine, spermine, or phenylalanine.

Example 3 High Leucine and Histidine (L+H) Amount Improves Clinical Parameters, Activity Function, and Lowers the Heart Failure-Related Rehospitalization Rate In the present invention, to demonstrate that supplying high leucine and histidine amount (L+H) increased the skeletal muscle mass, hemoglobin, and 6-minute walking distance, and lowered the heart failure-related event rate, better than supplying branch chain amino acids (BCAA) alone.

212 patients with heart failure (HF) were recruited. Enrollment criteria included patients (i) with typical signs and symptoms of HF and New York Heart Association (NYHA) functional classification II to IV, who were hospitalized due to acute cardiogenic pulmonary congestion based on chest x-rays (grade ≥I according to the classification by Battler et al.) after non-cardiogenic causes were excluded; (ii) with a left ventricular ejection fraction (LVEF) <40% documented by echocardiograms; and (iii) between 20 and 85 years of age. Exclusion criteria included (1) having a disorder other than HF that might compromise survival within the next six months; (2) having been bedridden for >3 months; (3) having a serum creatinine of ≥3 mg/dl; (4) having undergone dialysis within the previous two weeks; (5) having severe coronary artery disease without complete revascularization therapy; and (6) being pregnant.

212 HF patients divided into three groups: (1) the "L+H" group: patients' food was additionally supplied with high amounts of leucine (8.3±3.2 g/day) and histidine (1.5±0.5 g/day); (2) the branch chain amino acid (BCAA) group: patients' food was additionally supplied with BCAA (4.3±0.5 g of leucine/day, 2.2±0.3 g of isoleucine/day, and 4.4±0.4 g of valine/day); and (3) the control groups: no specific increase in their nutritional amount besides their usual intake. The nutrition was maintained for one month, and then, patients returned back to their usual intake.

Patients were followed up for the changes in their blood hemoglobin, B-type natriuretic peptide (BNP), albumin, leucine, and histidine levels, 6-min walking distance evaluation, skeletal muscle mass, and LVEF. BNP is a sensitive indicator of HF status (a higher value indicates a worse status). In addition, patients were also followed up clinically for HF-related re-hospitalization.

3.1 Laboratory Parameters

Blood samples were collected before discharge, and at each time point at designed schedule in EDTA-containing tubes. BNP was measured with the use of the Triage BNP Test (Biosite, San Diego, Calif., USA). The Triage BNP Test is a fluorescence immunoassay for the quantitative determination of BNP in plasma specimens. The mean of 3 determinations was taken. Other measurements including hemoglobin levels and albumin levels were conducted in our central laboratory.

3.2 Body Component Analyzer

Eight-polar bioimpedance analyses (BIA) of each participant were obtained using an Inbody 720 multi-frequency analyzer (at 1, 5, 50, 250, 500, and 1000 kHz) (Model Biospace In body 720, Seoul, Korea). In accordance with the manufacturer's guidelines, the measurement employed 8 contact electrodes (2 positioned on the palm and thumb, another 2 on the front part of the foot and heel) which enabled us to analyze 5 basic body parts (the left and right upper limbs, trunk, and left and right lower limbs) independently from each other. Patients were instructed to empty their stomach and bladder, avoid exercise, and recline for at least 5 min before the BIA measurement to increase the precision. All patients stood with their feet in contact with the foot electrode and grabbed the hand electrodes. The participant's identification number, height, age, and gender were entered into the analyzer. The electric current has a different penetration force depending on the frequency. By this way, skeletal muscle mass could be accurately evaluated at different time points in different groups of patients.

3.3 6-Min Walking Distance

To assess the functional level of each patient in different groups, walking distance in 6 minutes was evaluated by an experienced research nurse. This assessment can represent the health status and also the functional class of patients in response to different nutritional composition.

3.4 Cardiac Echocardiography

Echocardiographic images were obtained with patients in the left lateral decubitus position at end-expiration with 2.5 MHz (2-dimentional) (Philips iE33 machine). The left ventricular ejection fraction (LVEF) was calculated based on the Simpson method. The left ventricular end diastolic and systolic dimensions, and other associated anatomical abnormalities such as valvular lesions were estimated using the assessment suggested by the American Society of Echocardiography.

3.5 Patient Outcomes

Follow-up data were prospectively obtained every month from hospital records, personal communication with the patients' physicians, telephone interviews, and patients' regular visits to staff physician outpatient clinics. "Re-hospitalization" is defined as HF-related re-hospitalizations. HF-related re-hospitalization was analyzed for prognostic purposes.

3.6 Statistical Analysis

Results are expressed as the mean±SD for continuous variables and as the number (percentage) for categorical variables. Data were compared by unpaired t-tests, non-parametric tests, Chi-squared tests, Pearson correlations, or analysis of variance (ANOVA) followed by Tukey's post-hoc test, when appropriate. Follow-up data were collected as scheduled or at the last available visit. Kaplan-Meier curves were drawn and analyzed to compare the effect of different nutritional composition for patients with heart failure. All statistical analyses were two-sided and performed using SPSS software (version 15.0, SPSS, Chicago, Ill., USA). A p value of <0.05 was considered significant.

3.7 Results

In total, 212 hospitalized HF patients were eligible to participate in the study. The baseline characteristics of the three groups were shown in Table 1. There were no significant differences in age, sex, LVEF, functional class, incidence of co-morbidity, 6-min walking distance, or laboratory findings.

TABLE 1

Baseline characteristics of patients at hospital discharge (n = 212)

| Variable | Control n = 71 | BCAA n = 70 | L + H n = 71 |
|---|---|---|---|
| Age (years) | 61.7 ± 13.8 | 65.1 ± 12.6 | 62.7 ± 11.1 |
| Male (%) | 48 (67.6) | 44 (62.9) | 44 (62.0) |
| LVEF (%) | 28.0 ± 7.7 | 29.6 ± 6.9 | 29.0 ± 7.8 |
| New York Heart Association functional class | | | |
| II (%) | 22 (31.0) | 24 (34.3) | 28 (39.4) |
| III~IV (%) | 49 (69.1) | 46 (65.7) | 43 (60.6) |
| Blood pressure (mm Hg) | | | |
| Systolic | 126.8 ± 19.8 | 124.9 ± 17.9 | 122.1 ± 16.9 |
| Diastolic | 73.3 ± 14.0 | 74.1 ± 11.5 | 73.1 ± 12.4 |
| Heart rate, beats/min | 76.9 ± 11.2 | 77.4 ± 11.0 | 77.4 ± 13.1 |
| Co-morbidity | | | |
| Diabetes mellitus (%) | 33 (46.5) | 28 (40.0) | 34 (47.9) |
| Hypertension (%) | 44 (62.0) | 50 (71.4) | 46 (64.8) |
| Atrial fibrillation (%) | 19 (26.8) | 24 (34.3) | 21 (29.6) |
| COPD (%) | 4 (5.6) | 13 (18.6) | 8 (11.3) |
| Education | | | |
| Non (%) | 15 (21.1) | 23 (32.9) | 10 (14.1) |
| Eementary school (%) | 23 (32.4) | 22 (31.4) | 23 (32.4) |
| Junior high school (%) | 14 (19.5) | 8 (11.4) | 11 (15.5) |
| High school (%) | 19 (26.8) | 17 (24.3) | 27 (38.0) |
| Spouse (%) | 47 (66.2) | 43 (61.04) | 54 (76.1) |
| Body mass index (kg/m$^2$) | 25.2 ± 5.7 | 24.6 ± 5.3 | 25.9 ± 4.9 |
| 6-min walk (m) | 314 ± 110 | 313 ± 84 | 318 ± 83 |
| Laboratory values | | | |
| Serum sodium (mEq/L) | 139.0 ± 3.1 | 139.3 ± 3.0 | 138.9 ± 3.1 |
| eGFR (mg/dL) | 70.2 ± 32.6 | 70.9 ± 23.46 | 69.2 ± 24.7 |
| Hemoglobin (g/dL) | 13.2 ± 1.9 | 13.3 ± 1.8 | 13.0 ± 1.4 |
| BNP (g/dL) | 585 ± 517 | 575 ± 570 | 610 ± 713 |

TABLE 1-continued

Baseline characteristics of patients at hospital discharge (n = 212)

| Variable | Control<br>n = 71 | BCAA<br>n = 70 | L + H<br>n = 71 |
|---|---|---|---|
| Albumin (g/dL) | 3.5 ± 0.5 | 3.5 ± 0.5 | 3.5 ± 0.5 |
| Cholesterol (g/dL) | 172.6 ± 48.9 | 174.3 ± 51.6 | 176.5 ± 53.0 |
| Glycohemoglobin | 6.8 ± 1.9 | 6.5 ± 1.4 | 6.8 ± 1.5 |

BCAA, the group supported with branch-chain amino acid only;
L + H, the group supported with high amount of Leucine and Histidine;
BNP, B-type natriuretic peptide;
GFR, estimated glomerular filtration rate;
COPD, chronic obstructive pulmonary disease;
LVEF, left ventricular ejection fraction;
6-min walk, 6 minutes walking distance.

Changes in Clinical and Laboratory Parameters after One Month.

The plasma leucine levels were significantly decreased in the control group, were maintained at similar levels in the BCAA group, and were significantly increased in the L+H group. The plasma histidine levels were the same in the control and the BCAA group. However, there was a significant increase in the L+H group.

group was more remarkable than that in the BCAA group. And the present invention also validates that the therapeutically effective high amounts of leucine and histidine for improving a patient with heart failure is 4.0 g to 12.0 g leucine and 0.36 g to 2.4 g histidine per day, and the ratio of histidine:leucine is 1:5 to 1:11.

Rate of the Re-Hospitalization.

All patients were followed up for 6 months. As shown in FIGURE, the rates of HF-related re-hospitalization were 33.1%, 22.5% and 12.2% in the control, the BCAA, and the L+H groups, respectively. The Kaplan Meier curves showed that event-free survival rate in the BCAA group was insignificantly higher than the control group. However, the event-free survival rate was significant higher in the L+H group, compared to the control group (log rank=13.7, p=0.001).

In summary, the nutritional composition of the present invention with high dose of leucine and histidine is better in the view of some clinical and laboratory parameters, and 6-month event free survival.

TABLE 2

Clinical and laboratory data in 3 groups of patients

|  | Control (n = 71) | | BCAA (n = 70) | | L + H (n = 71) | | | |
|---|---|---|---|---|---|---|---|---|
|  | M0 | M1 | M0 | M1 | M0 | M1 | P value# | P value@ |
| 6-min walk (m) | 314 ± 110 | 326 ± 117 | 313 ± 84 | 345 ± 113* | 318 ± 83 | 391 ± 96* | NS | <0.05 |
| SMM (kg) | 22.5 ± 5.9 | 20.6 ± 5.3 | 21.3 ± 3.2 | 21.1 ± 3.3 | 22.8 ± 4.8 | 23.8 ± 5.2* | NS | <0.05 |
| LVEF (%) | 28.0 ± 7.7 | 29.2 ± 8.2* | 29.6 ± 6.9 | 33.9 ± 9.9* | 29.0 ± 7.8 | 36.8 ± 8.7* | NS | <0.05 |
| Hemoglobin (g/dL) | 13.2 ± 1.9 | 13.4 ± 1.6 | 13.3 ± 1.8 | 13.5 ± 1.5 | 13.0 ± 1.4 | 13.7 ± 1.7* | NS | <0.05 |
| Albumin (g/dL) | 3.5 ± 0.5 | 3.9 ± 0.5* | 3.5 ± 0.5 | 4.2 ± 0.4* | 3.5 ± 0.5 | 4.1 ± 0.4* | NS | NS |
| BNP (pg/ml) | 585 ± 517 | 667 ± 976 | 575 ± 570 | 244 ± 501* | 610 ± 713 | 104 ± 99* | <0.05 | <0.05 |

BCAA, the group supported with branch-chain amino acid only; L + H, the group supported with high amount of Leucine and Histidine; M0, data at baseline; M1, data measured 1 months later; 6-min walk, 6 minutes walking distance; SMM, skeletal muscle mass; LVEF, left ventricular ejection fraction; BNP, B-type natriuretic peptide.
*compared to data at M0;
the BCAA group compared to the control group regarding the difference between M0 and M1;
@the "L + H" group compared to the control group regarding the difference between M0 and M1.

In the control group, the distance of 6-min walking was insignificantly increased (Table 2). Both the BCAA and L+H group had significant increases in their 6-min walking distance. In addition, there was a trend that the increase was more in the L+H group than the BCAA group.

In skeletal muscle mass, there were no significant changes in the control and the BCAA groups. However, patients in the L+H group had a significant increase in their skeletal muscle mass (Table 2). Regarding the LVEF, only the L+H group had significant improvements. During the growth of skeletal muscle mass, the plasma level of histidine was transiently lowered in the first week for muscle synthesis in the L+H group. Histidine is important for the growth of skeletal muscle mass, and the improvement in cardiac contractility.

In hemoglobin level, there was a significant increase in the L+H group after one month. However, the increases in the control group and the BCAA group were insignificant. All three groups had significant increases in their plasma albumin levels. The increases were not different between these 3 groups. In BNP levels, the control group had an insignificant trend of increase at one month. Both the BCAA and the L+H groups had significant decreases in their BNP levels one month later. In addition, the decrease in the L+H Example 4 The Levels of Blood Acylcarnitines Increased after Supplying HF Patients with Medium-Chain Triglycerides In 35 patients with HF, the nutritional composition with medium-chain triglycerides was used for one month. As shown Table 3, blood examination for the metabolism of fatty acids was done by metabolomics analysis. The data showed that most of acylcarnitines (from short chain to long chain) were elevated in the blood, suggesting that the mitochondria of patients with HF had impaired beta-oxidation function, leading to the accumulation of a variety of acylcarnitines excreted out to the blood as waste.

TABLE 3

Lipid metabolites before and after supply with medium-chain triglycerides for one month in patients with heart failure (n = 35)

| Metabolite ID (μM) | Before | After | P-value |
|---|---|---|---|
| Octadecadienylcarnitine | 0.053 ± 0.034 | 0.105 ± 0.070 | <0.001 |
| Octadecenoylcarnitine | 0.122 ± 0.074 | 0.183 ± 0.102 | <0.001 |
| Butrylcarnitine | 0.233 ± 0.065 | 0.352 ± 0.230 | <0.001 |
| Decanoylcarnitine | 0.278 ± 0.117 | 0.218 ± 0.094 | 0.0020 |

TABLE 3-continued

Lipid metabolites before and after supply with medium-chain triglycerides for one month in patients with heart failure (n = 35)

| Metabolite ID (µM) | Before | After | P-value |
|---|---|---|---|
| Valerycarnitine | 0.101 ± 0.036 | 0.149 ± 0.121 | 0.0021 |
| Octanoylcarnitine | 0.197 ± 0.079 | 0.165 ± 0.056 | 0.0142 |
| Tetradecenoylcarnitine | 0.084 ± 0.057 | 0.110 ± 0.050 | 0.0097 |
| Propionylcarnitine | 0.357 ± 0.108 | 0.447 ± 0.268 | 0.0116 |
| Hexadecanoylcarnitine | 0.087 ± 0.043 | 0.112 ± 0.071 | 0.0199 |
| Decadienylcarnitine | 0.399 ± 0.126 | 0.342 ± 0.232 | 0.0836 |
| Tigloylcarnitine | 0.032 ± 0.019 | 0.036 ± 0.023 | 0.2839 |

Data are presented as mean ± SD.

These findings suggest that supplements with medium-chain triglycerides to patients with HF might be harmful.

Example 5 Supply the Sachet (Containing HF Formula) and Evaluate the Effect

A standard sachet of nutrition was developed, containing leucine (5.25 g), isoleucine (1.2 g), valine (2.25 g), and histidine (1.0 g) in each sachet. This formula is called the HF formula. Patients were divided into 2 groups: (1) HF formula group (n=12): patients took HF formula one sachet a day for 7 days and two sachets a day for another 7 days in addition to patients' regular intake; and (2) the control group (n=12): no additional nutritional supply.

A few laboratory parameters were monitored for 14 days, including plasma leucine, histidine and 3-methylhistidine levels. The level of plasma 3-methylhistidine indicates the amount of muscle protein breakdown. The measurement of these metabolites was based on the platform of LC-MS system.

In the plasma leucine level, there were no significant changes throughout the 14 days in the control group. Actually, there was a trend of decrease. In the HF formula group, the increase in the plasma leucine level was noted on the $7^{th}$ day, and was significant on the 14th day. In another embodiment, the HF formula included 28.0%-55.0% (w/w) leucine, 5.0%-10.0% (w/w) histidine, 6.8%-12.0% (w/w) isoleucine and 12.5%-23.0% (w/w) valine also showed the increased plasma leucine and histidine level.

In the plasma histidine level, there were no significant changes in the control group throughout the 14 days. However, there was a significant increase in the HF formula group on the $7^{th}$ and $14^{th}$ days. Regarding the 3-methylhistidine level, significant increase was noted on the $14^{th}$ day in the control group. The HF formula group had significant decreases in the 3-methylhistidine level on the $14^{th}$ day after supplied with nutrition containing HF formula. These findings suggested that nutritional composition in the HF formula significantly lowered the protein breakdown from skeletal muscles.

Example 6 High Leucine Amount Improved Clinical Parameters and Activity Function As a nutritional composition in addition to the food taken by patients with HF, three different compositions were given to the patients. Composition #1 group: histidine 1.0 g and leucine 5.0 g/day for 2 weeks and histidine 2.0 g and leucine 10.0 g/day for another 2 weeks; composition #2 group: histidine 1.0 g, leucine 2.0 g, isoleucine 1.0 g, and valine 2.0 g/day for 2 weeks and histidine 2.0 g, leucine 4.0 g, isoleucine 2.0 g, and valine 4.0 g/day for another 2 weeks; the group also represents branch chain amino acids (BCAA) supplemented with histidine; and composition #3 group: histidine 1.0 g and leucine 1.0 g/day for 2 weeks and histidine 2.0 g and leucine 2.0 g/day for another 2 weeks. Each group of patients was supported with additional nutrition for one month, and then returned back to their regular intake.

Patients with HF were supplied with 3 different compositions of nutrition. In composition #1 group, compared to the $0^{th}$ month (M0), patients at the first month after nutritional intervention (M1) had higher blood leucine and histidine levels. They also had higher blood albumin, and hemoglobin levels, but lower BNP levels; had a longer 6-min walking distance, increased skeletal muscle mass, and left ventricular ejection fraction (Table 4). In composition #2 group, compared to M0, patients at M1 had higher blood histidine levels, but the increase in leucine levels was insignificant. They had higher albumin levels, but lower BNP levels; however, the increase in hemoglobin levels was insignificant. Patients at M1 also had a longer 6-min walking distance; however, the increase in skeletal muscle mass and LVEF were not significant. In addition, compared to the composition #1 group, the composition #2 group had a less increase in the 6-min walking distance, and a less decrease in the BNP levels. The nutritional combination of high histidine and leucine amount is important for the growth of skeletal muscle mass, and the improvement in hemoglobin levels and cardiac contractility (Table 4).

In composition #3 group, compared to M0, patients at M1 had a higher blood albumin levels, but lower leucine levels; however, the levels in histidine, hemoglobin, and BNP levels were not significantly changed. Patients at M1 had an insignificant change in left ventricular ejection fraction. The changes in 6-min walking distance and skeletal muscle mass were also not significant. In addition, compared to the composition #1 group, the composition #3 group had less increases in histidine levels, 6-min walking distance, skeletal muscle mass, and left ventricular ejection fraction (Table 4).

TABLE 4

Clinical and laboratory data in 3 groups of patients

| | composition #1 group H + L(1:5) (n = 59) | | composition #2 group H + L + Iso + V (1:2:1:2) (n = 57) | | composition #3 group H + L(1:1) (n = 32) | | P value[#] | P value[@] |
|---|---|---|---|---|---|---|---|---|
| | M0 | M1 | M0 | M1 | M0 | M1 | | |
| 6-min walk (m) | 307 ± 86 | 382 ± 92* | 302 ± 88 | 332 ± 109* | 313 ± 112 | 324 ± 122 | <0.05 | <0.05 |
| SMM (kg) | 23.2 ± 4.5 | 24.1 ± 5.0* | 22.3 ± 3.4 | 22.5 ± 3.6 | 23.5 ± 6.0 | 21.6 ± 5.9 | NS | <0.05 |
| LVEF (%) | 21.7 ± 7.2 | 30.5 ± 8.6* | 24.7 ± 7.1 | 27.4 ± 8.2 | 23.8 ± 8.1 | 25.1 ± 7.8 | <0.05 | <0.05 |

TABLE 4-continued

Clinical and laboratory data in 3 groups of patients

| | composition #1 group H + L(1:5) (n = 59) | | composition #2 group H + L + Iso + V (1:2:1:2) (n = 57) | | composition #3 group H + L(1:1) (n = 32) | | P value# | P value@ |
|---|---|---|---|---|---|---|---|---|
| | M0 | M1 | M0 | M1 | M0 | M1 | | |
| Hemoglobin (g/dL) | 13.1 ± 1.4 | 13.9 ± 1.6* | 13.0 ± 1.7 | 13.2 ± 1.6 | 13.3 ± 1.8 | 13.4 ± 1.7 | NS | NS |
| Albumin (g/dL) | 3.5 ± 0.6 | 4.2 ± 0.4* | 3.5 ± 0.6 | 4.1 ± 0.5* | 3.5 ± 0.5 | 4.2 ± 0.4* | NS | NS |
| BNP (pg/ml) | 622 ± 674 | 106 ± 101* | 553 ± 620 | 237 ± 521* | 572 ± 525 | 617 ± 892 | <0.05 | <0.05 |

"composition #1 group": patients were supplied with histidine 1.0 g and leucine 5.0 g/day for 2 weeks and histidine 2.0 g and leucine 10.0 g/day for another 2 weeks; "composition #2 group": patients were supplied with histidine 1.0 g, leucine 2.0 g, isoleucine 1.0 g, and valine 2.0 g/day for 2 weeks and histidine 2.0 g, leucine 4.0 g, isoleucine 2.0 g, and valine 4.0 g/day for another 2 weeks; and "composition #3 group": patients were supplied with histidine 1.0 g and leucine 1.0 g/day for 2 weeks and histidine 2.0 g and leucine 2.0 g/day for another 2 weeks; M0, baseline; M1, 1 month after nutritional intervention; 6-min walk, 6 minutes walking distance; SMM, skeletal muscle mass; LVEF, left ventricular ejection fraction; BNP, B-type natriuretic peptide.
*compared to data at M0;
the "composition #2 group" group compared to the "composition #1 group" group regarding the difference between M0 and M1;
@the "composition #3 group" compared to the difference between M0 and M1 in the "composition #1 group" group

Example 7 High Histidine Amount Improves Clinical Parameters and Activity Function As a nutritional composition in addition to the food taken by patients with HF, two different compositions were given to the patients. Composition #4 group: histidine 1 g and leucine 5 g/day for 2 weeks and histidine 2 g and leucine 10 g/day for another 2 weeks; composition #5 group: histidine 0.25 g and leucine 5 g/day for 2 weeks and histidine 0.5 g and leucine 10 g/day for another 2 weeks. Each group of patients was supported with additional nutrition for one month, and then returned back to their regular intake.

In composition #4 group, compared to the $0^{th}$ month (M0), patients at the first month after nutritional intervention (M1) had higher blood leucine and histidine levels. They also had higher albumin and hemoglobin levels, but lower BNP levels; had a longer 6-min walking distance, increased skeletal mass, and left ventricular ejection fraction (Table 5). In composition #5 group, compared to M0, patients at M1 had higher blood leucine levels, but the level in histidine was not significantly changed. They had higher albumin levels, but lower BNP levels; however, the levels in hemoglobin levels were not significantly changed. Patients at M1 also had an increased 6-min walking distance (Table 5). However, there were no significant changes in skeletal muscle mass, or left ventricular ejection fraction. Furthermore, compared to the composition #4 group, the composition #5 group had less decreases in BNP levels, and less increase in 6-min walking distance (Table 5). Histidine is important for the growth of skeletal muscle mass, and the improvement in hemoglobin levels and cardiac contractility.

In the present invention, the therapeutically effective high amounts of leucine and histidine for improving a patient with heart failure is 4.0 g to 12.0 g leucine and 0.36 g to 2.4 g histidine per day, and the ratio of histidine:leucine is 1:5 to 1:11.

TABLE 5

Clinical and laboratory data in 2 groups of patients

| | H + L(1:5) (n = 59) | | H + L(0.25:5) (n = 31) | | P value# |
|---|---|---|---|---|---|
| | M0 | M1 | M0 | M1 | |
| 6-min walk (m) | 307 ± 86 | 382 ± 92* | 324 ± 86 | 375 ± 115* | NS |
| SMM (kg) | 23.2 ± 4.5 | 24.1 ± 5.0* | 21.5 ± 3.3 | 21.8 ± 3.2 | NS |
| LVEF (%) | 21.7 ± 7.2 | 30.5 ± 8.6* | 23.6 ± 6.8 | 25.0 ± 9.8 | <0.05 |
| Hemoglobin (g/dL) | 13.1 ± 1.4 | 14.0 ± 1.6* | 13.2 ± 1.7 | 13.4 ± 1.6 | <0.05 |
| Albumin (g/dL) | 3.5 ± 0.6 | 4.2 ± 0.4* | 3.5 ± 0.6 | 4.3 ± 0.5* | NS |
| BNP (pg/ml) | 622 ± 674 | 106 ± 101* | 586 ± 512 | 263 ± 473* | <0.05 |

"H + L(1:5)": patients were supplied with histidine 1 g and leucine 5 g/day for 2 weeks and histidine 2 g and leucine 10 g/day for another 2 weeks;
"H + L(0.25:5)": patients were supplied with histidine 0.25 g and leucine 5 g/day for 2 weeks and histidine 0.5 g and leucine 10 g/day for another 2 weeks;
M0, baseline;
M1, 1 month after nutritional intervention;
6-min walk, 6 minutes walking distance;
SMM, skeletal muscle mass;
LVEF, left ventricular ejection fraction;
BNP, B-type natriuretic peptide.
*compared to data at M0;
the "H + L(0.25:5)" group compared to the "H + L(1:5)" group regarding the difference between M0 and M1.

In summary, the present invention provides a nutritional composition for patient with heart failure consisting of the high amounts of leucine and histidine. The patients with heart failure are orally administered the nutritional composition containing 4.0 g to 12.0 g leucine and 0.36 g to 2.4 g histidine per day, and the ratio of histidine:leucine is 1:5 to 1:11. They will have a good outcome, such as symptoms, disease-related quality-of-life, and re-hospitalization rate in 6 months. Therefore, high amounts of leucine and histidine can be applied in the protection and treatment of heart failure. The present invention also provides a nutritional supplement to include the above-mentioned nutritional composition for patient with heart failure; it may be a beverage product, a dietary supplement or food.

What is claimed is:

1. A nutritional composition for improving a patient with heart failure, consisting of a therapeutically effective amount of leucine and histidine, wherein the ratio of histidine: leucine is 1:5 to 1:11, and the therapeutically effective amount of leucine is between 4.0 g and 12.0 g.

2. The nutritional composition of claim 1, wherein said improving a patient with heart failure includes increasing:

skeletal muscle mass, left ventricular ejection fraction, hemoglobin and 6-minute walking distance of said patient.

3. A nutritional supplement for improving a patient with heart failure comprising the nutritional composition of claim 1 and additional ingredients.

4. The nutritional supplement of claim 3, wherein the additional ingredients are isoleucine and valine.

5. The nutritional supplement of claim 4, wherein the nutritional composition is 33.0%-65.0% (w/w), isoleucine is 6.8%-12.0% (w/w), valine is 12.5%-23.0% (w/w) per unit dose of the nutritional supplement, the unit dose corresponding to per day.

6. The nutritional supplement of claim 3, wherein the ingredient is at least one selected from the group consisting of saccharide, mineral, vitamin, polyphenol, L-carnitine, Co-enzyme Q10, niacin and β-hydroxy-β-methylbutyrate (HMB).

7. The nutritional supplement of claim 6, wherein the saccharide is a β-glucan-like polysaccharide from *Auricularia polytricha* or giant kelp.

8. The nutritional supplement of claim 6, wherein the saccharide is an oligosaccharide, and the oligosaccharide is fructo-oligosaccharide.

9. The nutritional supplement of claim 6, wherein the polyphenol is resveratrol.

10. The nutritional supplement of claim 6, wherein the mineral is selected from the group consisting of calcium, magnesium, zinc, copper and selenium.

11. The nutritional supplement of claim 6, wherein the vitamin is selected from the group consisting of vitamin A, vitamin B6, vitamin B12, vitamin C, vitamin E, vitamin D, thiamine, riboflavin and folate.

12. The nutritional supplement of claim 3, wherein the nutritional supplement has no medium-chain triglycerides, tyrosine, spermidine, spermine, or phenylalanine.

13. The nutritional supplement of claim 3, wherein the nutritional supplement is in a form selected from the group consisting of powder, liquid, and ready-to use.

14. A method of improving a heart failure in a patient, comprising administering to the patient a nutritional supplement comprising a therapeutically effective amount of the nutritional composition of claim 1 and additional ingredients.

15. The method of claim 14, wherein the nutritional supplement is administered orally per day.

16. The method of claim 14, wherein the patient is suffering acute or chronic heart failure.

17. The method of claim 14, wherein when administered to the patient, the nutritional supplement increases the skeletal muscle mass, the left ventricular ejection fraction, hemoglobin and the 6-minute walking distance.

18. The method of claim 14, wherein the additional ingredients are isoleucine and valine.

19. The method of claim 18, wherein the nutritional composition is 33.0%-65.0% (w/w), isoleucine is 6.8%-12.0% (w/w), valine is 12.5%-23.0% (w/w) per unit dose of the nutritional supplement, the unit dose corresponding to per day.

20. The method of claim 14, wherein the ingredient is at least one selected from the group consisting of polysaccharide, mineral, vitamin, polyphenol, L-carnitine, Co-enzyme Q10, niacin and β-hydroxy-β-methylbutyrate (HMB).

21. The method of claim 14, wherein the nutritional supplement has no medium-chain triglycerides, tyrosine, spermidine, spermine, or phenylalanine.

* * * * *

UNITED STATES PATENT AND TRADEMARK OFFICE
CERTIFICATE OF CORRECTION

PATENT NO. : 9,730,916 B2  
APPLICATION NO. : 14/631620  
DATED : August 15, 2017  
INVENTOR(S) : Chao-Hung Wang, Ming-Shi Shiao and Mei-Ling Cheng Page 1 of 1

It is certified that error appears in the above-identified patent and that said Letters Patent is hereby corrected as shown below:

On the Title Page

Item (73) the correct assignee should be both:  
Chang Gung Memorial Hospital, Keelung Keelung City, TAIWAN  
-And-  
Chang Gung University Taoyuan City, TAIWAN Signed and Sealed this  
Second Day of October, 2018

Andrei Iancu  
*Director of the United States Patent and Trademark Office*